United States Patent
He et al.

(10) Patent No.: US 9,580,448 B2
(45) Date of Patent: Feb. 28, 2017

(54) BORON ESTER FUSED THIOPHENE MONOMERS

(71) Applicant: Corning Incorporated, Corning, NY (US)

(72) Inventors: Mingqian He, Horseheads, NY (US); James Robert Matthews, Painted Post, NY (US); Weijun Niu, Painted Post, NY (US); Arthur Lawrence Wallace, Corning, NY (US)

(73) Assignee: Corning Incorporated, Corning, NY (US)

( * ) Notice: Subject to any disclaimer, the term of this patent is extended or adjusted under 35 U.S.C. 154(b) by 6 days.

(21) Appl. No.: 14/721,485

(22) Filed: May 26, 2015

(65) Prior Publication Data

US 2015/0252062 A1 Sep. 10, 2015

Related U.S. Application Data

(62) Division of application No. 14/460,649, filed on Aug. 15, 2014, now Pat. No. 9,070,882.

(60) Provisional application No. 61/868,720, filed on Aug. 22, 2013.

(51) Int. Cl.

| C07D 495/14 | (2006.01) |
|---|---|
| C07F 5/02 | (2006.01) |
| C07D 495/22 | (2006.01) |
| H01L 51/00 | (2006.01) |
| C08L 65/00 | (2006.01) |
| C08G 61/12 | (2006.01) |
| H01L 51/05 | (2006.01) |
| H01L 51/42 | (2006.01) |

(52) U.S. Cl.
CPC .............. *C07F 5/02* (2013.01); *C07D 495/14* (2013.01); *C07D 495/22* (2013.01); *C07F 5/025* (2013.01); *C08G 61/124* (2013.01); *C08G 61/126* (2013.01); *C08L 65/00* (2013.01); *H01L 51/008* (2013.01); *H01L 51/0036* (2013.01); *H01L 51/0043* (2013.01); *H01L 51/0068* (2013.01); *H01L 51/0074* (2013.01); *C08G 2261/1412* (2013.01); *C08G 2261/3243* (2013.01); *C08G 2261/344* (2013.01); *C08G 2261/411* (2013.01); *H01L 51/0053* (2013.01); *H01L 51/0545* (2013.01); *H01L 51/4253* (2013.01)

(58) Field of Classification Search
CPC .......... C07D 495/14; H01L 51/00; C07F 5/02
USPC .......................................................... 549/4
See application file for complete search history.

(56) References Cited

U.S. PATENT DOCUMENTS

| 7,919,634 | B2 | 4/2011 | He et al. |
|---|---|---|---|
| 8,278,346 | B2 | 10/2012 | He et al. |
| 8,278,410 | B2 | 10/2012 | He et al. |
| 8,349,998 | B2 | 1/2013 | He |
| 8,754,241 | B2 | 6/2014 | Yamada et al. |
| 8,846,855 | B2 | 9/2014 | He et al. |
| 8,982,443 | B2 | 3/2015 | Yamada et al. |
| 9,070,882 | B2 * | 6/2015 | He et al. |
| 2012/0035375 | A1 | 2/2012 | He et al. |
| 2012/0314272 | A1 | 12/2012 | Yamada et al. |
| 2013/0058256 | A1 | 3/2013 | Li et al. |
| 2013/0100517 | A1 | 4/2013 | Yamada et al. |

(Continued)

OTHER PUBLICATIONS

He et al.; "Alkylsubstituted Thienothiophene Semiconducting Meterials: Structure-Property Relationships"; J. Am. Chem. Soc. (2009), 131; pp. 11930-11938.

(Continued)

*Primary Examiner* — Golam M M Shameem
(74) *Attorney, Agent, or Firm* — Jason A. Barron

(57) ABSTRACT

A compound of formula (I), formula (II), or a combination thereof, and salts thereof is described.

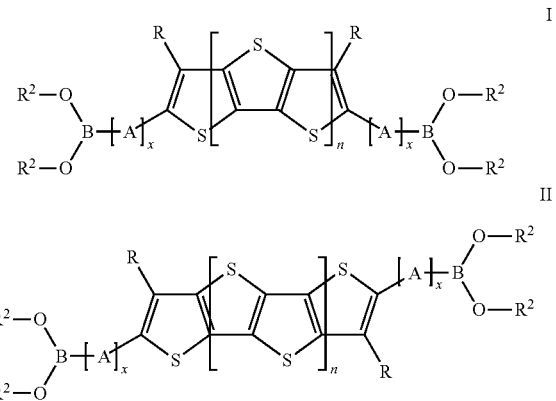

Each A may be independently an optionally substituted conjugated species or an optionally substituted aromatic species. Each R may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3.

4 Claims, No Drawings

(56) References Cited

U.S. PATENT DOCUMENTS

2013/0109821 A1    5/2013   He et al.

OTHER PUBLICATIONS

Okada et al.; "Improvement of the redox stability of dithieno[3,2-b:2',3'-d] thiophene derivatives by using bulky substituents"; Journal of Molecular Structure 1037 (2013); pp. 256-263.
Park et al.; "Acene-Containing Donor-Acceptor Conjugated Polymers: Correlation between the Structure of Donor Moiety, Charge Carrier Mobility, and Charge Transport Dynamics in Electronic Devices"; American Chemical Society, Macromolecules (2014), 47; pp. 3747-3754.
Stanetty et al.; "Halogenated 2'-Chlorobithiazoles via Pd-Catalyzed Cross-Coupling Reactions"; J. Org. Chem. (2006), 71; pp. 3754-3761.
Yu et al.; "Evaluation of Heterocycle-Modified Pentathiophene-Based Molecular Donor Materials for Solar Cells"; American Chemical Society, Appl. Mater. Interfaces (2014), 6; pp. 5798-5809.
European Patent Office; International Search Report; Mail Date: Feb. 3, 2015; pp. 1-9.
International Search Report and Written Opinion of the International Searching Authority; PCT/US2014/051776; Mailed February 3, 2015; 28 Pages.
Louis F. Fieser and Mary Fieser, Reagents for Organic Synthesis, v. 1-19, Wiley, New York (1967-1999 ed.).

* cited by examiner

BORON ESTER FUSED THIOPHENE MONOMERS

CROSS REFERENCES TO RELATED APPLICATIONS

This application is a divisional of and claims the benefit of priority to U.S. patent application Ser. No. 14/460,649, filed on Aug. 15, 2014, which claims the benefit of priority under 35 U.S.C. §119 of U.S. Provisional Application Ser. No. 61/868,720, filed on Aug. 22, 2013, the contents of which are relied upon and incorporated herein by reference in their entireties.

FIELD

The following description relates to compositions including boron ester fused thiophene monomers and, more particularly, to methods for directly substituting boron esters onto fused thiophenes and methods for making polymers and extended conjugation small molecules therefrom.

BACKGROUND

Highly conjugated organic materials, due to their interesting electronic and optoelectronic properties, are being investigated for use in a variety of applications, including organic semiconductors (OSCs), field effect transistors (FETs), thin-film transistors (TFTs), organic light-emitting diodes (OLEDs), electro-optic (EO) applications, as conductive materials, as two photon mixing materials, as organic semiconductors, and as non-linear optical (NLO) materials.

In particular, OSCs have attracted a great amount of attention in the research community due to their advantages over inorganic semiconductors such as exhibiting a high mechanical flexibility, producing at low cost, and having a low weight. Polycyclic aromatic compounds, such as oligothiophenes, acenes, phthalocyanenes, and polythiophene, have been widely studied as semiconductor materials.

In addition, fused thiophene polymers synthesized by Stille coupling have been recognized as promising in the area of highly conjugated polymers. These fused thiophene polymers include a series of β-, β'-alkyl substituted fused thiophene ditin monomer materials. To this end, there has been a desire to develop new chemistry in order to produce different monomers for creation of potentially useful fused thiophene based polymers.

SUMMARY

In the examples described herein, a new class of fused thiophene based boron-substituted monomer species, in which boron esters are directly substituted onto fused thiophenes, has been developed to allow Suzuki coupling to be used in place of Stille coupling to form fused thiophene based polymers and extended small molecules. In addition, synthetic methods are described herein for the making of this new class of organic compounds. Further, new and potentially advantageous methods are described herein for the use of this new class of organic compounds to make other polymers and extended conjugation small monomers. Moreover, boron compounds, such as the fused thiophene based boron-substituted monomer species described herein, generally have lower toxicity than tin compounds, such as those previously recognized with respect to fused thiophene based ditin monomers. The use of boron in the compounds herein avoids tin usage in material making.

In a first general aspect, a compound may include formula (I), formula (II), or a combination thereof, and salts thereof

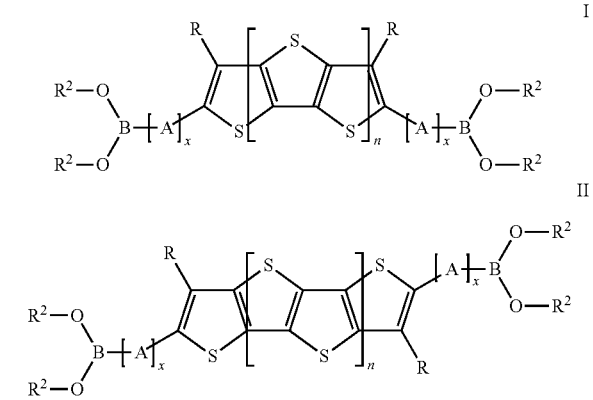

Each A may be independently an optionally substituted conjugated species or an optionally substituted aromatic species. Each R may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3.

The compound may consist of formula (I) and salts thereof.

The compound may consist of formula (II) and salts thereof.

The optionally substituted conjugated species may be one selected from the group consisting of ethylene, butadiene, and acetylene.

The optionally substituted aromatic species may be one selected from the group consisting of benzene, naphthalene, anthracene, pyrene, thiophene, pyrrole, porphyrins, carbazoles, furan, indole, and fused thiophenes.

Each R and $R^2$ may be independently an optionally substituted $C_6$-$C_{24}$ linear alkyl chain.

Each R and $R^2$ may be independently an optionally substituted $C_{13}$-$C_{19}$ linear alkyl chain.

The optionally substituted alkyl chain containing heteroatoms may be one selected from the group consisting of oligo(ethylene glycol), oligo(propylene glycol), and oligo(ethylene diamine).

The substituted alkyl chains may include ketone, amine, ester, one or more unsaturations, halide, nitro, aldehyde, hydroxyl, carboxylic acid, alkoxy, or any combination thereof.

Each x may be independently less than or equal to 1.

Each x may be equal to 0.

The first aspect may be provided alone or in combination with any one or more of the examples of the first aspect discussed above.

In a second general aspect, a method of making a compound of formula (I) and salts thereof is described.

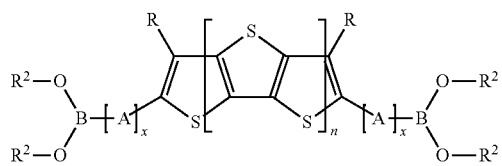

I

The method may include reacting a compound of formula (III)

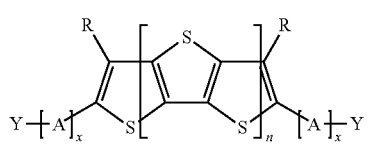

III with an alkyl lithium to give an intermediate, and reacting the intermediate with a compound of formula (IV)

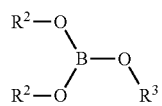

IV to give the compound of formula (I). Each A may be independently an optionally substituted conjugated species or an optionally substituted aromatic species. Each R and $R^3$ may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3.

The optionally substituted conjugated species may be one selected from the group consisting of ethylene, butadiene, and acetylene.

The optionally substituted aromatic species may be one selected from the group consisting of benzene, naphthalene, anthracene, pyrene, thiophene, pyrrole, porphyrins, carbazoles, furan, indole, and fused thiophenes.

Each R, $R^2$, and $R^3$ may be independently an optionally substituted $C_6$-$C_{24}$ linear alkyl chain.

Each R, $R^2$, and $R^3$ may be independently an optionally substituted $C_{13}$-$C_{19}$ linear alkyl chain.

The optionally substituted alkyl chain containing heteroatoms may be one selected from the group consisting of oligo(ethylene glycol), oligo(propylene glycol), and oligo(ethylene diamine).

The substituted alkyl chains may include ketone, amine, ester, one or more unsaturations, halide, nitro, aldehyde, hydroxyl, carboxylic acid, alkoxy, or any combination thereof.

Each x may be independently less than or equal to 1.

Each x may be equal to 0.

The second aspect may be provided alone or in combination with any one or more of the examples of the second aspect discussed above.

In a third general aspect, a method of making a compound of formula (II) and salts thereof is described.

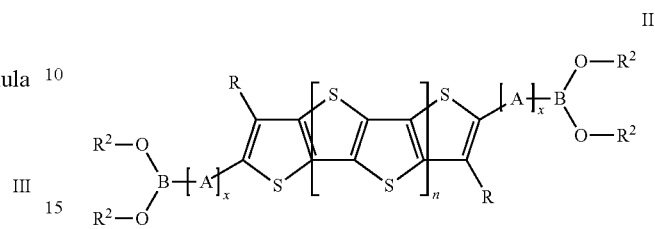

II

The method may include reacting a compound of formula (V)

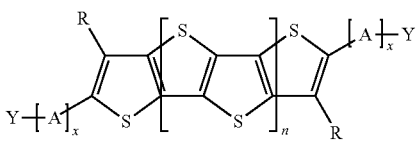

V with an alkyl lithium to give an intermediate, and reacting the intermediate with a compound of formula (IV)

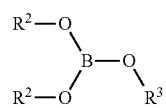

IV to give the compound of formula (II). Each A may be independently an optionally substituted conjugated species or an optionally substituted aromatic species. Each R and $R^3$ may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3.

The optionally substituted conjugated species may be one selected from the group consisting of ethylene, butadiene, and acetylene.

The optionally substituted aromatic species may be one selected from the group consisting of benzene, naphthalene, anthracene, pyrene, thiophene, pyrrole, porphyrins, carbazoles, furan, indole, and fused thiophenes.

Each R, $R^2$, and $R^3$ may be independently an optionally substituted $C_6$-$C_{24}$ linear alkyl chain.

Each R, $R^2$, and $R^3$ may be independently an optionally substituted $C_{13}$-$C_{19}$ linear alkyl chain.

The optionally substituted alkyl chain containing heteroatoms may be one selected from the group consisting of oligo(ethylene glycol), oligo(propylene glycol), and oligo(ethylene diamine).

The substituted alkyl chains may include ketone, amine, ester, one or more unsaturations, halide, nitro, aldehyde, hydroxyl, carboxylic acid, alkoxy, or any combination thereof.

Each x may be independently less than or equal to 1.
Each x may be equal to 0.
The third aspect may be provided alone or in combination with any one or more of the examples of the third aspect discussed above.

In a fourth general aspect, a method of making a compound of formula (VI) and salts thereof is described.

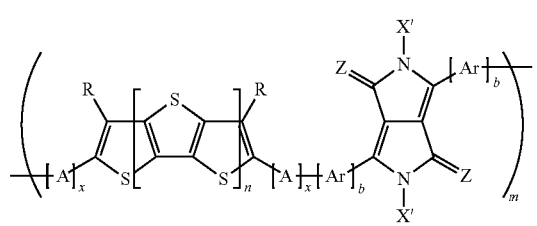

VI

The method may include reacting a compound of formula (I)

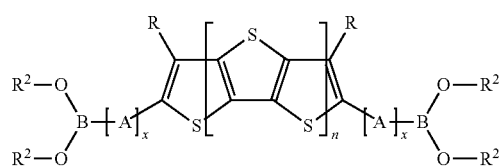

I with a compound of formula (VII)

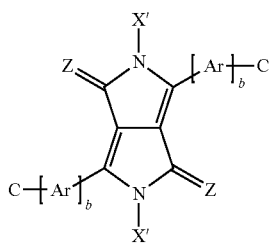

VII in the presence of a metal catalyst to give the compound of formula (VI). Each A and Ar may be independently an optionally substituted conjugated species or an optionally substituted aromatic species. Each R and X' may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3. Each b may be independently less than or equal to 5 and greater than or equal to 1. Each Z may be independently O, S, Se, or substituted imines.

Each C may be independently selected from the group consisting of Br, Cl, and I. m may be in a range of 1 to 100.

The metal catalyst may be selected from the group consisting of Pt, Pd, Ru, and Rh.

Each b may be equal to 1.

Each Z may be independently O, S, or substituted imines.

The optionally substituted conjugated species may be one selected from the group consisting of ethylene, butadiene, and acetylene.

The optionally substituted aromatic species may be one selected from the group consisting of benzene, naphthalene, anthracene, pyrene, thiophene, pyrrole, porphyrins, carbazoles, furan, indole, and fused thiophenes.

Each R, $R^2$, and X' may be independently an optionally substituted $C_6$-$C_{24}$ linear alkyl chain.

Each R, $R^2$, and X' may be independently an optionally substituted $C_{13}$-$C_{19}$ linear alkyl chain.

The optionally substituted alkyl chain containing heteroatoms may be one selected from the group consisting of oligo(ethylene glycol), oligo(propylene glycol), and oligo(ethylene diamine).

The substituted alkyl chains may include ketone, amine, ester, one or more unsaturations, halide, nitro, aldehyde, hydroxyl, carboxylic acid, alkoxy, or any combination thereof.

Each x may be independently less than or equal to 1.
Each x may be equal to 0.
m may be in the range of 1 to 50.
Each Z may be O.

The fourth aspect may be provided alone or in combination with any one or more of the examples of the fourth aspect discussed above.

In a fifth general aspect, a method of making a compound of formula (VIII) and salts thereof is described.

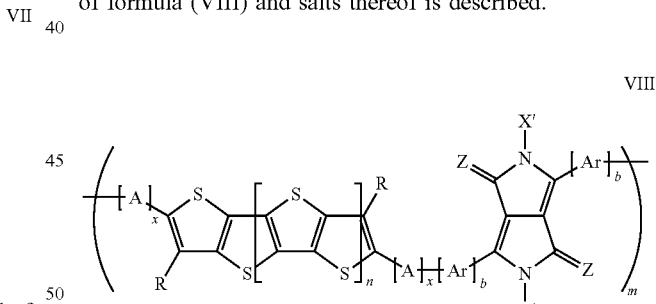

VIII

The method may include reacting a compound of formula (II)

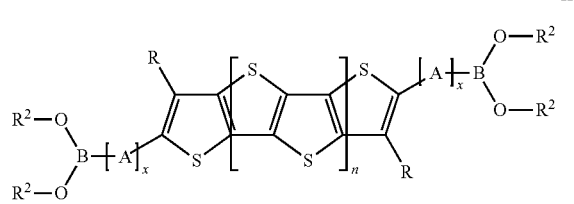

II with a compound of formula (VII)

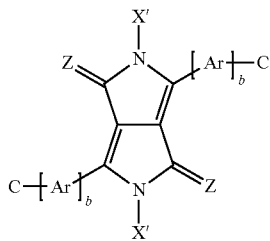

VII in the presence of a metal catalyst to give the compound of formula (VIII). Each A and Ar may be independently an optionally substituted conjugated species or an optionally substituted aromatic species. Each R and X' may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3. Each b may be independently less than or equal to 5 and greater than or equal to 1. Each Z may be independently O, S, Se, or substituted imines. Each C may be independently selected from the group consisting of Br, Cl, and I. m may be in a range of 1 to 100.

The metal catalyst may be selected from the group consisting of Pt, Pd, Ru, and Rh.

Each b may be equal to 1.

Each Z may be independently O, S, or substituted imines.

The optionally substituted conjugated species may be one selected from the group consisting of ethylene, butadiene, and acetylene.

The optionally substituted aromatic species may be one selected from the group consisting of benzene, naphthalene, anthracene, pyrene, thiophene, pyrrole, porphyrins, carbazoles, furan, indole, and fused thiophenes.

Each R, $R^2$, and X' may be independently an optionally substituted $C_6$-$C_{24}$ linear alkyl chain.

Each R, $R^2$, and X' may be independently an optionally substituted $C_{13}$-$C_{19}$ linear alkyl chain.

The optionally substituted alkyl chain containing heteroatoms may be one selected from the group consisting of oligo(ethylene glycol), oligo(propylene glycol), and oligo(ethylene diamine).

The substituted alkyl chains may include ketone, amine, ester, one or more unsaturations, halide, nitro, aldehyde, hydroxyl, carboxylic acid, alkoxy, or any combination thereof.

Each x may be independently less than or equal to 1.

Each x may be equal to 0.

m may be in the range of 1 to 50.

Each Z may be O.

The fifth aspect may be provided alone or in combination with any one or more of the examples of the fifth aspect discussed above.

DETAILED DESCRIPTION

The claimed invention may be embodied in many different forms and should not be construed as limited to the example embodiments set forth herein. These example embodiments are provided so that this disclosure will be both thorough and complete, and will fully convey the scope of the claimed invention to those skilled in the art.

Before the present materials, articles, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

The term "alkyl" refers to a monoradical branched or unbranched saturated hydrocarbon chain having a variable amount of carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to: (1) an alkyl group as defined above, having 1, 2, 3, 4 or 5 substituents, typically 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_p$R$_{SO}$, where R$_{SO}$ is alkyl, aryl, or heteroaryl and p is 0, 1 or 2; or (2) an alkyl group as defined above that is interrupted by 1-10 atoms independently chosen from oxygen, sulfur and $NR_a$, where $R_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or $—S(O)_pR_{SO}$, in which $R_{SO}$ is alkyl, aryl, or heteroaryl and p is 0, 1 or 2; or (3) an alkyl group as defined above that has both 1, 2, 3, 4 or 5 substituents as defined above and is also interrupted by 1-10 atoms as defined above.

The term "alkoxy" refers to the group D-O—, where D is an optionally substituted alkyl or optionally substituted cycloalkyl, or D is a group —Y—W, in which Y is optionally substituted alkylene and W is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, typically 1-10 carbon atoms, more typically 1, 2, 3, 4, 5 or 6 carbon atoms. This term is exemplified by groups such as methylene ($—CH_2—$), ethylene ($—CH_2CH_2—$), the propylene isomers (e.g., $—CH_2CH_2CH_2—$ and $—CH(CH_3)CH_2—$) and the like.

The term "substituted alkylene" refers to: (1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, $—SO_2$-alkyl, $—SO_2$-aryl and $—SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and $—S(O)_pR_{SO}$, where $R_{SO}$ is alkyl, aryl, or heteroaryl and p is 0, 1 or 2; or (2) an alkylene group as defined above that is interrupted by 1-20 atoms independently chosen from oxygen, sulfur and $NR_a$—, where $R_a$ is chosen from hydrogen, optionally substituted alkyl, cycloalkyl, cycloalkenyl, aryl, heteroaryl and heterocyclyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene ($—CH(NH_2)CH_2—$), methylaminoethylene ($—CH(NHMe)CH_2—$), 2-carboxypropylene isomers ($—CH_2CH(CO_2H)CH_2—$), ethoxyethyl ($—CH_2CH_2O—CH_2CH_2—$), ethylmethylaminoethyl ($—CH_2CH_2N(CH_3)CH_2CH_2—$), and the like.

The term "alkylthio" refers to the group $R_s$—S—, where $R_s$ is as defined for alkoxy.

The term "alkenyl" refers to a monoradical of a branched or unbranched unsaturated hydrocarbon group typically having from 2 to 20 carbon atoms, more typically 2 to 10 carbon atoms and even more typically 2 to 6 carbon atoms and having 1-6, typically 1, double bond (vinyl). Typical alkenyl groups include ethenyl or vinyl ($—CH=CH_2$), 1-propylene or allyl ($—CH_2CH=CH_2$), isopropylene ($—C(CH_3)=CH_2$), bicyclo[2.2.1]heptene, and the like. In the event that alkenyl is attached to nitrogen, the double bond cannot be alpha to the nitrogen.

The term "substituted alkenyl" refers to an alkenyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, $—SO_2$-alkyl, $SO_2$-aryl and $—SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and $—S(O)_pR_{SO}$, where $R_{SO}$ is alkyl, aryl, or heteroaryl and p is 0, 1 or 2.

The term "alkynyl" refers to a monoradical of an unsaturated hydrocarbon, typically having from 2 to 20 carbon atoms, more typically 2 to 10 carbon atoms and even more typically 2 to 6 carbon atoms and having at least 1 and typically from 1-6 sites of acetylene (triple bond) unsaturation. Typical alkynyl groups include ethynyl, ($—C≡CH$), propargyl (or prop-1-yn-3-yl, $—CH_2C≡CH$), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, $—SO_2$-alkyl, $SO_2$-aryl and $—SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and $—S(O)_pR_{SO}$, where $R_{SO}$ is alkyl, aryl, or heteroaryl and p is 0, 1 or 2.

The term "aminocarbonyl" refers to the group —C(O)$NR_NR_N$ where each $R_N$ is independently hydrogen, alkyl, aryl, heteroaryl, heterocyclyl or where both $R_N$ groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and $—S(O)_pR_{SO}$, where $R_{SO}$ is alkyl, aryl, or heteroaryl and p is 0, 1 or 2.

The term "acylamino" refers to the group $—NR_{NCO}C(O)R$ where each $R_{NCO}$ is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF₃, amino, substituted amino, cyano, and —S(O)$_p$R$_{SO}$, where R$_{SO}$ is alkyl, aryl, or heteroaryl and p is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF₃, amino, substituted amino, cyano, and —S(O)$_p$R$_{SO}$, where R$_{SO}$ is alkyl, aryl, or heteroaryl and p is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Typical aryls include phenyl, naphthyl and the like.

Unless otherwise constrained by the definition for the aryl substituent, such aryl groups can optionally be substituted with from 1 to 5 substituents, typically 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF₃, amino, substituted amino, cyano, and —S(O)$_p$R$_{SO}$, where R$_{SO}$ is alkyl, aryl, or heteroaryl and p is 0, 1 or 2.

The term "aryloxy" refers to the group aryl-O— wherein the aryl group is as defined above, and includes optionally substituted aryl groups as also defined above. The term "arylthio" refers to the group aryl-S—, where aryl is as defined as above.

The term "amino" refers to the group —NH₂.

The term "substituted amino" refers to the group —NR$_w$R$_w$ where each R$_w$ is independently selected from the group consisting of hydrogen, alkyl, cycloalkyl, carboxyalkyl (for example, benzyloxycarbonyl), aryl, heteroaryl and heterocyclyl provided that both R$_w$ groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF₃, amino, substituted amino, cyano, and —S(O)$_p$R$_{SO}$, where R$_{SO}$ is alkyl, aryl, or heteroaryl and p is 0, 1 or 2.

The term "carboxyalkyl" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, CF₃, amino, substituted amino, cyano, and —S(O)$_p$R$_{SO}$, in which R$_{SO}$ is alkyl, aryl, or heteroaryl and p is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethyl bicyclo[2.2.1]hept-2-yl, (2,3,3-trimethylbicyclo[2.2.1]hept-2-yl), or carbocyclic groups to which is fused an aryl group, for example indane, and the like.

The term "cycloalkenyl" refers to carbocyclic groups of from 3 to 20 carbon atoms having a single cyclic ring or multiple condensed rings with at least one double bond in the ring structure.

The terms "substituted cycloalkyl" or "substituted cycloalkenyl" refer to cycloalkyl or cycloalkenyl groups having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF₃, amino, substituted amino, cyano, and —S(O)$_p$R$_{SO}$, where R$_{SO}$ is alkyl, aryl, or heteroaryl and p is 0, 1 or 2.

The term "halogen" or "halo" refers to fluoro, bromo, chloro, and iodo.

The term "acyl" denotes a group —C(O)R$_{CO}$, in which R$_{CO}$ is hydrogen, optionally substituted alkyl, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, triazole, oxazole, thiazole, naphthyridine, and the like as well as N-oxide and N-alkoxy derivatives of nitrogen containing heteroaryl compounds, for example pyridine-N-oxide derivatives.

Unless otherwise constrained by the definition for the heteroaryl substituent, such heteroaryl groups can be optionally substituted with 1 to 5 substituents, typically 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO— alkyl, —SO-aryl, —SO— heteroaryl, —SO₂-alkyl, SO₂-aryl and —SO₂-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and $—S(O)_p R_{SO}$, where $R_{SO}$ is alkyl, aryl, or heteroaryl and p is 0, 1 or 2.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, typically 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclyl substituent, such heterocyclyl groups can be optionally substituted with 1, 2, 3, 4 or 5, and typically 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, al koxyamino, nitro, —SO-alkyl, —SO-aryl, —SO-heteroaryl, —$SO_2$-alkyl, —$SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and $—S(O)_p R_{SO}$, where $R_{SO}$ is alkyl, aryl, or heteroaryl and p is 0, 1 or 2.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group $—S(O)R_{SO}$, in which $R_{SO}$ is alkyl, aryl, or heteroaryl. "Substituted sulfoxide" refers to a group $—S(O)R_{SO}$, in which $R_{SO}$ is substituted alkyl, substituted aryl, or substituted heteroaryl, as defined herein.

The term "sulfone" refers to a group $—S(O)_2R_{SO}$, in which $R_{SO}$ is alkyl, aryl, or heteroaryl. "Substituted sulfone" refers to a group $—S(O)_2R_{SO}$, in which $R_{SO}$ is substituted alkyl, substituted aryl, or substituted heteroaryl, as defined herein.

The term "keto" refers to a group —C(O)—.

The term "thiocarbonyl" refers to a group —C(S)—.

The term "carboxy" refers to a group —C(O)OH.

The term "conjugated group" or "conjugated species" is defined as a linear, branched or cyclic group, or combination thereof, in which p-orbitals of the atoms within the group are connected via delocalization of electrons and wherein the structure can be described as containing alternating single and double or triple bonds and may further contain lone pairs, radicals, or carbenium ions. Conjugated cyclic groups may comprise both aromatic and non-aromatic groups, and may comprise polycyclic or heterocyclic groups, such as diketopyrrolopyrrole. Ideally, conjugated groups are bound in such a way as to continue the conjugation between the thiophene moieties they connect.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Embodiments described herein may include a new class of fused thiophene based boron-substituted monomer species, in which boron esters are directly substituted onto fused thiophenes, has been developed to allow Suzuki coupling to be used in place of Stille coupling to form fused thiophene based polymers and extended small molecules. In addition, synthetic methods may be described herein for the making of this new class of organic compounds. Further, new and potentially advantageous methods may be described herein for the use of this new class of organic compounds to make other polymers and extended conjugation small monomers. Moreover, boron compounds, such as the fused thiophene based boron-substituted monomer species described herein, generally may have lower toxicity than tin compounds, such as those previously recognized with respect to fused thiophene based ditin monomers. The use of boron in the compounds herein may avoid tin usage in material making.

In a first general aspect, a compound may include formula (I), formula (II), or a combination thereof, and salts thereof

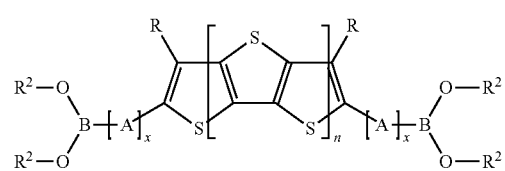

-continued

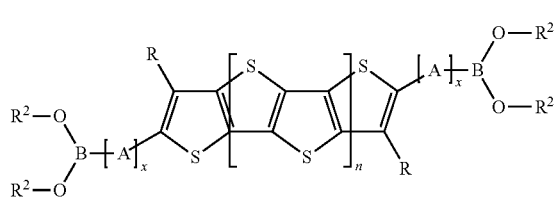

II

Each A may be independently an optionally substituted conjugated species or an optionally substituted aromatic species. Each R may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3.

In some embodiments, the compound may consist of formula (I) and salts thereof or formula (II) and salts thereof. In some embodiments, the optionally substituted conjugated species may be one selected from the group consisting of ethylene, butadiene, and acetylene. In some embodiments, the optionally substituted aromatic species may be one selected from the group consisting of benzene, naphthalene, anthracene, pyrene, thiophene, pyrrole, porphyrins, carbazoles, furan, indole, and fused thiophenes. In some embodiments, each R and $R^2$ may be independently an optionally substituted $C_6$-$C_{24}$ linear alkyl chain. In some embodiments, each R and $R^2$ may be independently an optionally substituted $C_{13}$-$C_{19}$ linear alkyl chain. In some embodiments, the optionally substituted alkyl chain containing heteroatoms may be one selected from the group consisting of oligo(ethylene glycol), oligo(propylene glycol), and oligo(ethylene diamine). In some embodiments, the substituted alkyl chains may include ketone, amine, ester, one or more unsaturations, halide, nitro, aldehyde, hydroxyl, carboxylic acid, alkoxy, or any combination thereof. In some embodiments, each x may be independently less than or equal to 1. In some embodiments, each x may be equal to 0.

For example, the first general aspect may include embodiments such as the compounds of formulas (IX), (X), (XI), and (XII). Each R may be independently an optionally substituted $C_1$-$C_{40}$ linear alkyl chain, an optionally substituted branched alkyl chain, an optionally substituted alkyl chain containing heteroatoms, substituted alkyl chains, or H. Each X may be independently C or N. Each Ar may be independently an optionally substituted conjugated species or an optionally substituted aromatic species.

IX

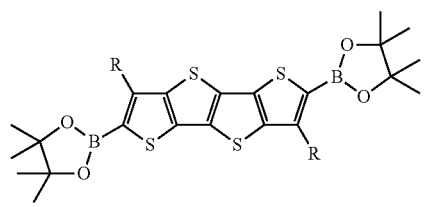

X

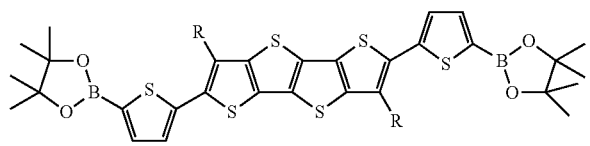

XI

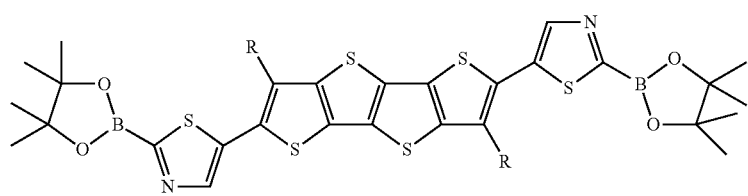

XII

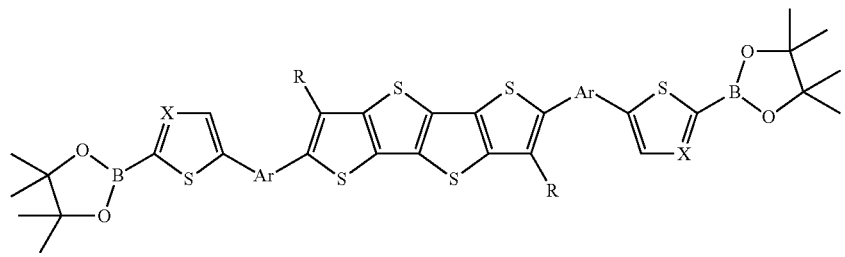

In other general aspects, embodiments may be produced through a series of synthetic steps. For example, the second and third aspects described below may depict potential routes for synthesizing the above-referenced embodiments of the first general aspect. The fourth and fifth aspects described below may depict potential routes for synthesizing polymers using the compounds of the above-referenced embodiments of the first general aspect. The methods disclosed herebelow are intended for purposes of exemplifying only and are not to be construed as limitations thereon.

Those skilled in the art will appreciate that other synthetic routes may be used to synthesize the inventive compounds. Some aspects of some embodiments may be synthesized by synthetic routes that include processes analogous to those well-known in the chemical arts, particularly in light of the description contained herein. Although specific starting materials and reagents are depicted in the schemes and discussed below, other starting materials and reagents can be easily substituted to provide a variety of derivatives and/or reaction conditions. The starting materials are generally available from commercial sources, such as Aldrich Chemicals (Milwaukee, Wis.), or are readily prepared using methods well known to those skilled in the art (e.g., prepared by methods generally described in Louis F. Fieser and Mary Fieser, REAGENTS FOR ORGANIC SYNTHESIS, V. 1-19, Wiley, New York (1967-1999 ed.), or BEILSTEINS HANDBUCH DER ORGANISCHEN CHEMIE, 4, Aufl. ed. Springer-Verlag, Berlin, including supplements (also available via the Beilstein online database)). In addition, many of the compounds prepared by the methods described below can be further modified in light of this disclosure using conventional chemistry well known to those skilled in the art.

In a second general aspect, a compound of formula (I) and salts thereof may be synthesized.

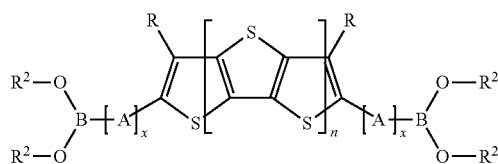

I

The method of synthesis may include reacting a compound of formula (III) with an alkyl lithium to give an intermediate, and reacting the intermediate with a compound of formula (IV) to give the compound of formula (I)

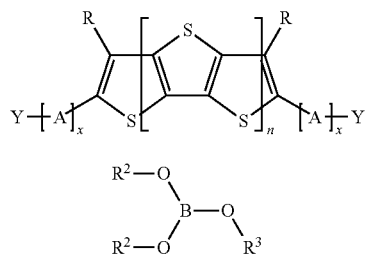

III

IV

Each A may be independently an optionally substituted conjugated species or an optionally substituted aromatic species. Each R and $R^3$ may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3.

In some embodiments, the optionally substituted conjugated species may be one selected from the group consisting of ethylene, butadiene, and acetylene. In some embodiments, the optionally substituted aromatic species may be one selected from the group consisting of benzene, naphthalene, anthracene, pyrene, thiophene, pyrrole, porphyrins, carbazoles, furan, indole, and fused thiophenes. In some embodiments, each R, $R^2$, and $R^3$ may be independently an optionally substituted $C_6$-$C_{24}$ linear alkyl chain. In some embodiments, each R, $R^2$, and $R^3$ may be independently an optionally substituted $C_{13}$-$C_{19}$ linear alkyl chain. In some embodiments, the optionally substituted alkyl chain containing heteroatoms may be one selected from the group consisting of oligo(ethylene glycol), oligo(propylene glycol), and oligo(ethylene diamine). In some embodiments, the substituted alkyl chains may include ketone, amine, ester, one or more unsaturations, halide, nitro, aldehyde, hydroxyl, carboxylic acid, alkoxy, or any combination thereof. In some embodiments, each x may be independently less than or equal to 1. In some embodiments, each x may be equal to 0.

In a third general aspect, a compound of formula (II) and salts thereof may be synthesized.

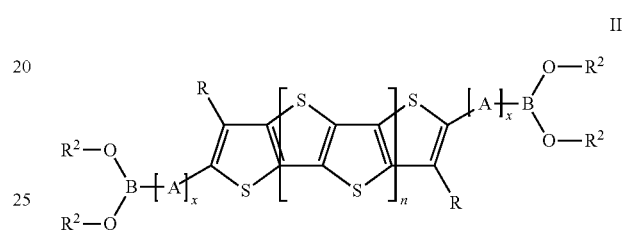

II

The method may include reacting a compound of formula (V) with an alkyl lithium to give an intermediate, and reacting the intermediate with a compound of formula (IV) to give the compound of formula (II).

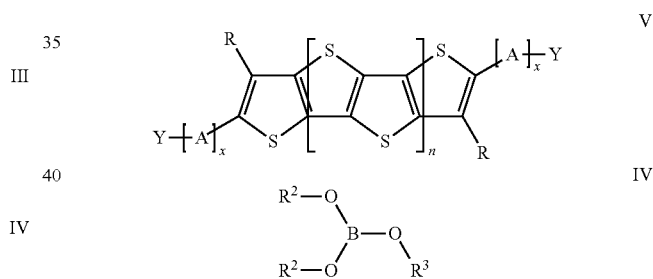

V

IV

Each A may be independently an optionally substituted conjugated species or an optionally substituted aromatic species. Each R and $R^3$ may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3.

In some embodiments, the optionally substituted conjugated species may be one selected from the group consisting of ethylene, butadiene, and acetylene. In some embodiments, the optionally substituted aromatic species may be one selected from the group consisting of benzene, naphthalene, anthracene, pyrene, thiophene, pyrrole, porphyrins, carbazoles, furan, indole, and fused thiophenes. In some embodiments, each R, $R^2$, and $R^3$ may be independently an optionally substituted $C_6$-$C_{24}$ linear alkyl chain. In some embodiments, each R, $R^2$, and $R^3$ may be independently an optionally substituted $C_{13}$-$C_{19}$ linear alkyl chain. In some embodiments, the optionally substituted alkyl chain containing heteroatoms may be one selected from the group consisting of oligo(ethylene glycol), oligo(propylene glycol), and oligo(ethylene diamine). In some embodiments, the substituted alkyl chains may include ketone, amine, ester, one or more unsaturations, halide, nitro, aldehyde, hydroxyl, carboxylic acid, alkoxy, or any combination thereof. In some embodiments, each x may be independently less than or equal to 1. In some embodiments, each x may be equal to 0.

The second and third general aspects and embodiments thereof may be used to synthesize examples illustrated in Schemes 1 and 2 depicted below.

Scheme 1

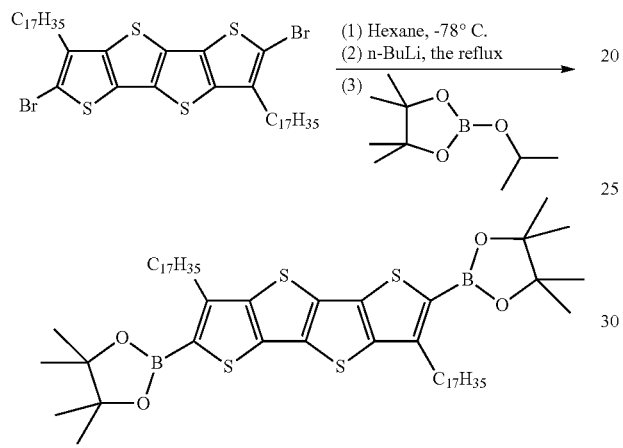

Scheme 2

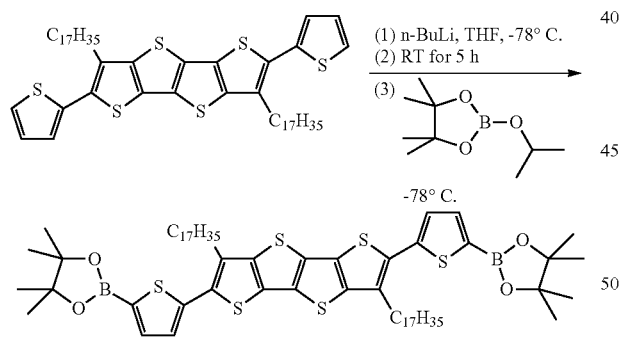

In Scheme 1, 3.8 mL (9.2 mmol) of n-butyl lithium (2.4 M in hexane) was added dropwise to 3.50 g (3.95 mmol) of the compound of formula (XIII) in 120 mL of anhydrous hexane at −78° C.

XIII

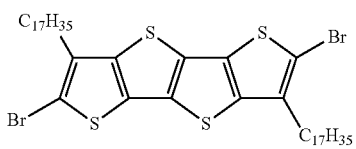

The reaction mixture was then warmed to room temperature then refluxed for a period of four hours. The reaction mixture was subsequently cooled to −78° C., after which 1.83 g (2.01 mL, 9.86 mmol) of 2-isopropoxy-4,4,5,5-tetramethyl-1,3,2-dioxaborolane was added dropwise. The cloudy reaction mixture was then warmed to room temperature and stirred for a period of eight hours. 100 mL of ice water was subsequently added into the cloudy solution and an additional 200 mL of hexane was then added. This mixture was shaken, after which the hexane layer was collected under reduced pressure to yield a solid residue that was subsequently dissolved in 500 mL of hot acetone. A hot filtration was then carried out, and the filtrate was cooled slowly to room temperature. Colorless crystals that formed from the filtrate were collected by filtration and recrystallized several times from acetone to form 2.70 g of the compound of Formula (XIV) as colorless crystals at 70% yield.

XIV

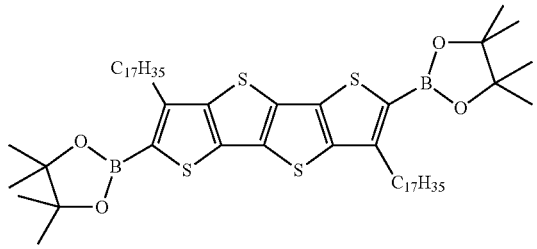

In Scheme 2, 3.1 mL (7.78 mmol) of n-butyl lithium (2.5 M in hexane) was added dropwise to 2 g (2.24 mmol) of the compound of formula (XV) in 200 mL of anhydrous tetrahydrofuran at −78° C.

XV

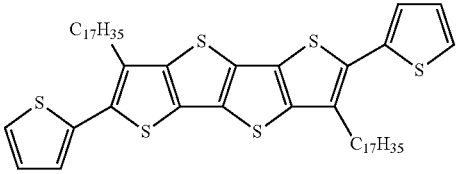

The resulting solution was stirred at room temperature for four hours. It was then cooled to −78° C., after which 1.04 g (8.28 mmol) of 2-isopropoxy-4,4,5,5-tetramethyl-1,3,2-dioxaborolane was added dropwise. The cloudy reaction mixture was warmed to room temperature and stirred for eight hours. 100 mL of ice-water was added into the cloudy mixture, and the tetrahydrofuran was removed under reduced pressure to yield a light yellowish solid in an aqueous suspension. The solid was filtered from the aqueous phase, dissolved in ethyl acetate, washed by water, and dried over anhydrous $Na_2SO_4$. After the evaporation of solvent, the residue was recrystallized from 20 mL of ethyl acetate to form 0.89 g of the compound of formula (XVI) as a light yellowish solid at 35% yield.

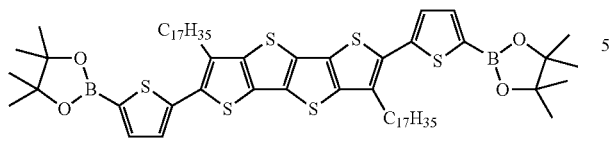

XVI

Schemes 3 and 4 depicted below are comparative examples of related art synthetic methods in which the desired product was not formed.

Scheme 3

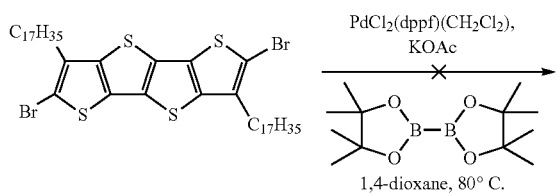

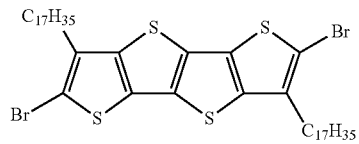

XIII

A nitrogen gas stream was flushed through the flask for five minutes, after which, under nitrogen protection, 40 mL of anhydrous 1,4-dioxane was added. Nitrogen was bubbled through the solution for ten minutes and the flask was then transferred to a glovebox. In the glovebox, 0.238 g (0.292 mmol) of $PdCl_2(dppf)(CH_2Cl_2)$ was added into the flask ("dppf" is a common abbreviation for 1,1'-bis(diphenylphosphino)ferrocene $C_{34}H_{28}FeP_2$). The flask was then taken out of the glovebox, kept under nitrogen, and heated at 80° C. for twenty hours. $^1H$ NMR of the crude product did not show any of the desired product of formula (XIV).

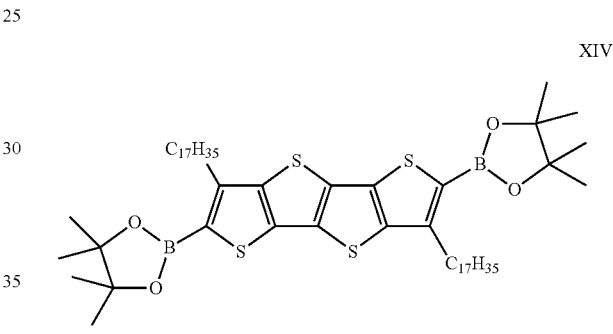

XIV

The crude product was purified by a short-path silica gel column chromatography (hot ethyl acetate/hexane as the eluent). No desired product was obtained after purification.

In Scheme 4, 1.14 mL (2.85 mmol) of n-BuLi (2.5 M in hexane) was added dropwise under nitrogen protection to 1.15 g (1.30 mmol) of the compound of formula (XIII) in 40 mL of anhydrous THF in a flask fitted with a stir bar at −78° C.

Scheme 4

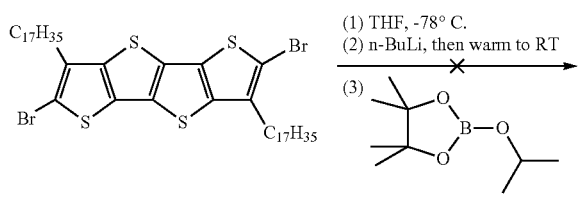

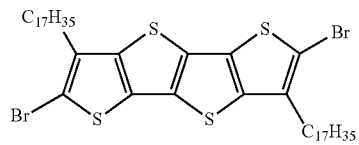

XIII

The resulting solution was stirred at room temperature for four hours. It was then cooled to −78° C. again and 0.53 g (2.85 mmol) of 2-isopropoxy-4,4,5,5-tetramethyl-1,3,2-dioxaborolane was added dropwise. The cloudy reaction solution was warmed to room temperature and stirred overnight. 100 mL of ice water was added into the cloudy solution and THF was then removed under reduced pressure to yield a greyish solid that was collected by filtration. $^1H$ NMR of the dried greyish solid in hot $CDCl_2CDCl_2$ showed only the compound of formula (XIII).

In Scheme 3, 1.48 g (1.67 mmol) of the compound of formula (XIII), 1.017 g (4.004 mmol) of bis(pinacolato) diboron, and 0.959 g of potassium acetate were added to a three neck flask fitted with a stir bar.

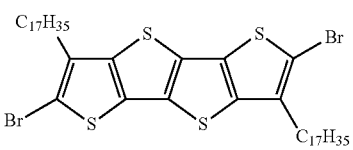

XIII

In a fourth general aspect, a compound of formula (VI) and salts thereof may be synthesized.

VI

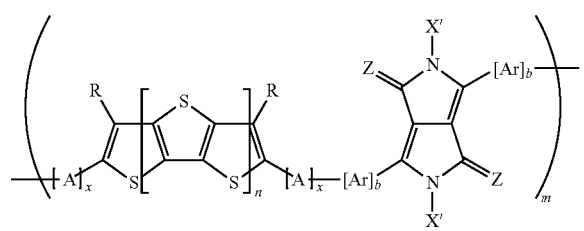

The method of synthesis may include reacting a compound of formula (I) with a compound of formula (VII) in the presence of a metal catalyst to give the compound of formula (VI).

I

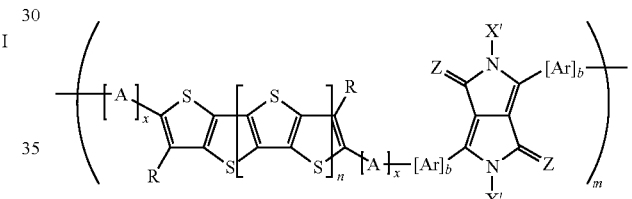

VII

Each A and Ar may be independently an optionally substituted conjugated species or an optionally substituted aromatic species. Each R and X' may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3. Each b may be independently less than or equal to 5 and greater than or equal to 1. Each Z may be independently O, S, Se, or substituted imines. Each C may be independently selected from the group consisting of Br, Cl, and I. m may be in a range of 1 to 100.

In some embodiments, the metal catalyst may be selected from the group consisting of Pt, Pd, Ru, and Rh. In some embodiments, each b may be equal to 1. In some embodiments, each Z may be independently O, S, or substituted imines. In some embodiments, the optionally substituted conjugated species may be one selected from the group consisting of ethylene, butadiene, and acetylene. In some embodiments, the optionally substituted aromatic species may be one selected from the group consisting of benzene, naphthalene, anthracene, pyrene, thiophene, pyrrole, porphyrins, carbazoles, furan, indole, and fused thiophenes. In some embodiments, each R, $R^2$, and X' may be independently an optionally substituted $C_6$-$C_{24}$ linear alkyl chain. In some embodiments, each R, $R^2$, and X' may be independently an optionally substituted $C_{13}$-$C_{19}$ linear alkyl chain. In some embodiments, the optionally substituted alkyl chain containing heteroatoms may be one selected from the group consisting of oligo(ethylene glycol), oligo(propylene glycol), and oligo(ethylene diamine). In some embodiments, the substituted alkyl chains may include ketone, amine, ester, one or more unsaturations, halide, nitro, aldehyde, hydroxyl, carboxylic acid, alkoxy, or any combination thereof. In some embodiments, each x may be independently less than or equal to 1. In some embodiments, each x may be equal to 0. In some embodiments, m may be in the range of 1 to 50. In some embodiments, each Z may be O.

In a fifth general aspect, a compound of formula (VIII) and salts thereof may be synthesized.

VIII

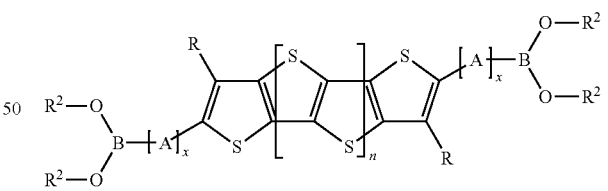

The method of synthesis may include reacting a compound of formula (II) with a compound of formula (VII) in the presence of a metal catalyst to give the compound of formula (VIII).

II

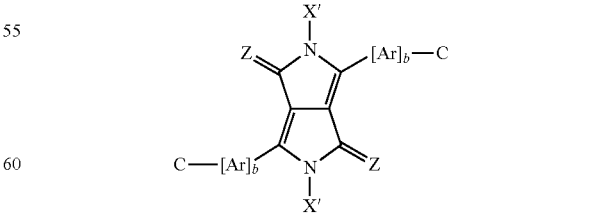

VII

Each A and Ar may be independently an optionally substituted conjugated species or an optionally substituted aromatic species. Each R and X' may be independently an optionally substituted $C_1$-$C_{40}$ linear alkyl chain, an optionally substituted branched alkyl chain, an optionally substituted alkyl chain containing heteroatoms, substituted alkyl chains, or H. Each $R^2$ may be independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with an other $R^2$. Each n may be independently less than or equal to 3 and greater than or equal to 1. Each x may be independently less than or equal to 3. Each b may be independently less than or equal to 5 and greater than or equal to 1. Each Z may be independently O, S, Se, or substituted imines. Each C may be independently selected from the group consisting of Br, Cl, and I. m may be in a range of 1 to 100.

In some embodiments, the metal catalyst may be selected from the group consisting of Pt, Pd, Ru, and Rh. In some embodiments, each b may be equal to 1. In some embodiments, each Z may be independently O, S, or substituted imines. In some embodiments, the optionally substituted conjugated species may be one selected from the group consisting of ethylene, butadiene, and acetylene. In some embodiments, the optionally substituted aromatic species may be one selected from the group consisting of benzene, naphthalene, anthracene, pyrene, thiophene, pyrrole, porphyrins, carbazoles, furan, indole, and fused thiophenes. In some embodiments, each R, $R^2$, and X' may be independently an optionally substituted $C_6$-$C_{24}$ linear alkyl chain. In some embodiments, each R, $R^2$, and X' may be independently an optionally substituted $C_{13}$-$C_{19}$ linear alkyl chain. In some embodiments, the optionally substituted alkyl chain containing heteroatoms may be one selected from the group consisting of oligo(ethylene glycol), oligo(propylene glycol), and oligo(ethylene diamine). In some embodiments, the substituted alkyl chains may include ketone, amine, ester, one or more unsaturations, halide, nitro, aldehyde, hydroxyl, carboxylic acid, alkoxy, or any combination thereof. In some embodiments, each x may be independently less than or equal to 1. In some embodiments, each x may be equal to 0. In some embodiments, m may be in the range of 1 to 50. In some embodiments, each Z may be O.

The fourth and fifth general aspects may be used to synthesize examples illustrated in Schemes 5 and 6 depicted below. n may be in a range of 1 to 100 or, for example, 1 to 50. Each R may be independently an optionally substituted $C_1$-$C_{40}$ linear alkyl chain, an optionally substituted branched alkyl chain, an optionally substituted alkyl chain containing heteroatoms, substituted alkyl chains, or H. Each Ar may be independently an optionally substituted conjugated species or an optionally substituted aromatic species.

Scheme 5

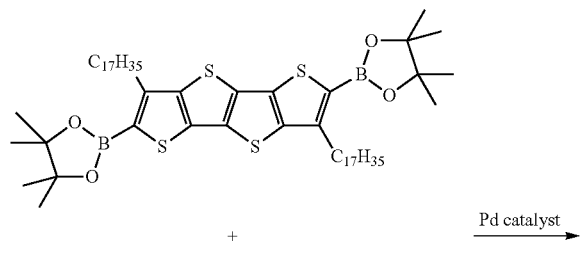

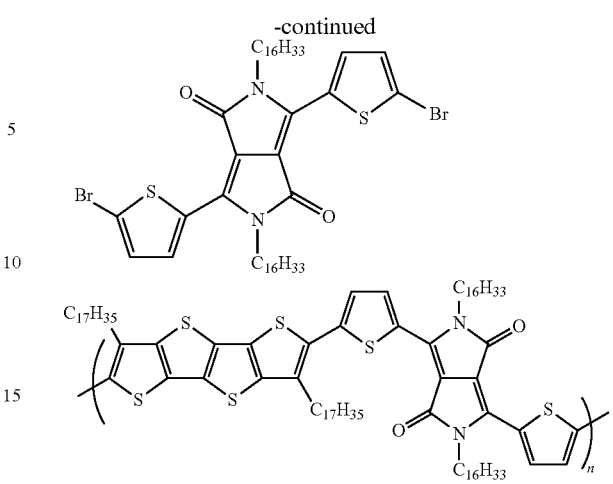

Scheme 6

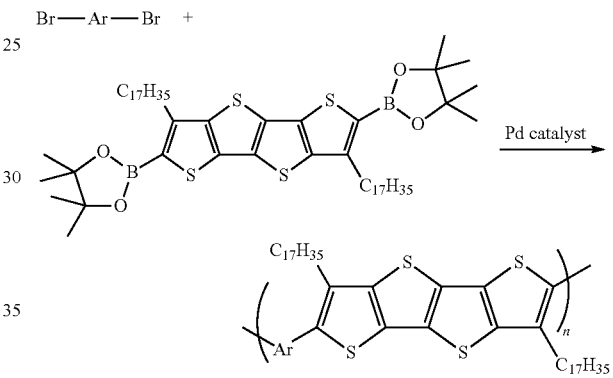

For example, in Scheme 5, 333 mg (0.34 mmol) of 2,6-di(4,4,5,5-tetramethyl-1,3,2-dioxaborolan-2-yl)-3,7-diheptadecylthieno[3,2-b]thieno[2',3':4,5]thieno[2,3-d]thiophene, 308 mg (0.34 mmol) of 3,6-bis(5-bromothiophen-2-yl)-2,5-dihexadecylpyrrolo[3,4-c]pyrrole-1,4-dione, 10 mL of toluene, 5 mL of pre-degassed water, and 0.3 mL of Aliquat 336 were added to a 2 neck round bottom flask equipped with a magnetic stir bar. A condenser and septum were then fitted to the flask necks. Nitrogen was subsequently bubbled through the mixture (via needle through the septum and outlet through the condenser) for thirty minutes, before 15.6 mg (17.0 µmol) of tris(dibenzylideneacetone)dipalladium(0) and 20.7 mg (68.0 µmol) of o-tolyl phosphine were added. Nitrogen bubbling was then continued for ten minutes. The mixture was subsequently heated at 95° C. for 3 days, controlled by directly immersing a thermocouple in the reaction mixture via the septum. The mixture was then cooled to room temperature and poured into 100 mL of ethanol, after which the mixture was stirred for sixteen hours. The mixture was then filtered with the resultant polymer being placed into a glass with glass frit Soxhlet thimble. The polymer was subsequently washed in a Soxhlet apparatus with 250 mL of acetone twenty-four hours. The polymer was then extracted from the Soxhlet apparatus into 250 mL of chloroform. The chloroform solution was subsequently poured into 400 mL of methanol with rapid stirring, followed by moderate stirring for twenty minutes. The polymer was then filtered from the mixture and dried under vacuum to give 200 mg of the product, poly[(3,7-diheptadecylthieno[3,2-b]thieno[2',3':4,5]thieno[2,3-d]thiophene-2,6-diyl)[2,5-dihexadecyl-3,6-di(thiophen-2-yl)pyrrolo[3,4-c]pyrrole-1,4-dione]-5,5'-diyl] at 40% yield as a blue solid.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A method of making a compound of formula (I) and salts thereof,

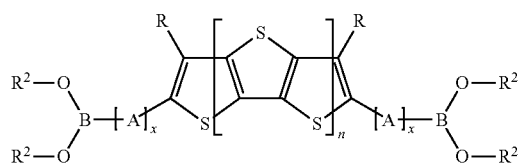

I the method comprising:
reacting a compound of formula (III)

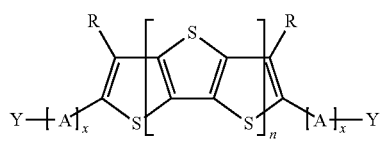

III with an alkyl lithium to give an intermediate; and
reacting the intermediate with a compound of formula (IV)

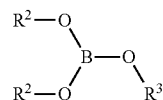

IV to give the compound of formula (I),
wherein each A is independently an optionally substituted conjugated species or an optionally substituted aromatic species,
wherein each R and $R^3$ is independently an optionally substituted $C_1$-$C_{40}$ linear alkyl chain, an optionally substituted branched alkyl chain, an optionally substituted alkyl chain containing heteroatoms, substituted alkyl chains, or H,
wherein each $R^2$ is independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with another $R^2$,
wherein each n is independently less than or equal to 3 and greater than or equal to 1, and
wherein each x is independently less than or equal to 3.

2. The method of claim 1, wherein each x is independently less than or equal to 1.

3. A method of making a compound of formula (II) and salts thereof,

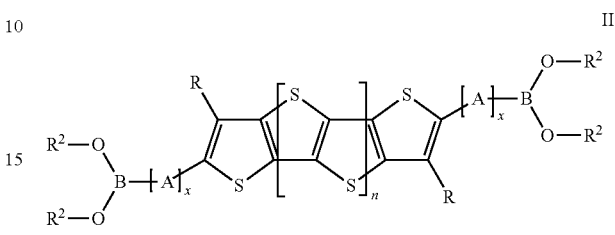

II the method comprising:
reacting a compound of formula (V)

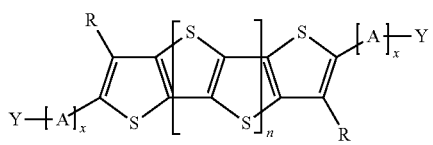

V with an alkyl lithium to give an intermediate; and
reacting the intermediate with a compound of formula (IV)

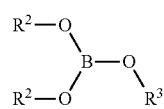

IV to give the compound of formula (II),
wherein each A is independently an optionally substituted conjugated species or an optionally substituted aromatic species,
wherein each R and $R^3$ is independently an optionally substituted $C_1$-$C_{40}$ linear alkyl chain, an optionally substituted branched alkyl chain, an optionally substituted alkyl chain containing heteroatoms, substituted alkyl chains, or H,
wherein each $R^2$ is independently an optionally substituted $C_1$-$C_{40}$ linear alkyl chain, an optionally substituted branched alkyl chain, an optionally substituted alkyl chain containing heteroatoms, substituted alkyl chains, H, or part of a cyclic boronate ester with another $R^2$,
wherein each n is independently less than or equal to 3 and greater than or equal to 1, and
wherein each x is independently less than or equal to 3.

4. The method of claim 3, wherein each x is independently less than or equal to 1.

* * * * *